United States Patent [19]
Bottcher et al.

[11] Patent Number: 5,693,655
[45] Date of Patent: Dec. 2, 1997

[54] 3-INDOLYLPIPERIDINES

[75] Inventors: Henning Bottcher, Darmstadt; Joachim Marz, Mainz; Christoph Seyfried, Jugenheim; Hartmut Greiner, Darmstadt; Gerd Bartoszyk, Weiterstadt, all of Germany

[73] Assignee: Merck Patent Gesellschaft Mit Beschrankter Haftung, Darmstadt, Germany

[21] Appl. No.: 426,405

[22] Filed: Apr. 21, 1995

[30] Foreign Application Priority Data

Apr. 22, 1994 [DE] Germany ............... 44 14 113.0

[51] Int. Cl.$^6$ .................. A61K 31/445; C07D 401/14
[52] U.S. Cl. .................. 514/323; 546/201
[58] Field of Search .................. 546/201; 514/323

[56] References Cited

FOREIGN PATENT DOCUMENTS

| 0 058 975 | 9/1982 | European Pat. Off. |
| 2 675 801 | 10/1992 | France. |
| 2 044 254 | 10/1980 | United Kingdom. |
| 2 184 444 | 6/1987 | United Kingdom. |

*Primary Examiner*—C. Warren Ivy
*Assistant Examiner*—Garth M. Dahlen
*Attorney, Agent, or Firm*—Millen, White, Zelano & Branigan, P.C.

[57] ABSTRACT

3-Indolylpiperidines of the formula I

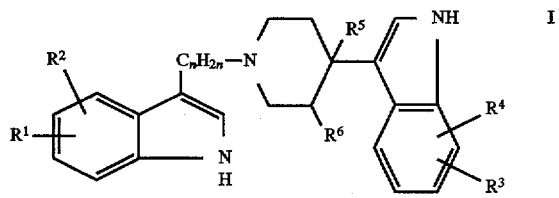

wherein $R^1$, $R^2$, $R^3$ and $R^4$ are in each case independently of one another H, A, OH, OA, F, Cl, Br, Z, CN, CF$_3$, COOH, CONH$_2$, CONHA, CONA$_2$, or COOA, or $R^1$ and $R^2$ and also $R^3$ and $R^4$ in each case together are also methylenedioxy, $R^5$ is H or OH, $R^6$ is H or $R^5$ and $R^6$ together are also a bond, A is alkyl having 1 to 6 C atoms and n is 2, 3, 4, 5 or 6, and to their physiologically acceptable salts, exhibit action on the central nervous system, in particular dopamine-agonistic or dopamine-antagonistic action.

16 Claims, No Drawings ved
3-INDOLYLPIPERIDINES

BACKGROUND OF THE INVENTION

The invention relates to 3-indolylpiperidines of the formula I wherein
$R^1$, $R^2$, $R^3$ and $R^4$ are in each case independently of one another H, A, OH, OA, F, Cl, Br, I, CN, $CF_3$, COOH, $CONH_2$, CONHA, $CONA_2$ or COOA, or $R^1$ and $R^2$ and also $R^3$ and $R^4$ in each case together are also methylenedioxy, $R^5$ is H or OH, $R^6$ is H or $R^5$ and $R^6$ together are also a bond, A is alkyl having 1 to 6 C atoms and n is 2, 3, 4, 5 or 6, and to their physiologically acceptable salts.

An object of the invention was to find novel compounds capable of being used for the preparation of drugs.

Upon further study of the specification and appended claims, further objects and advantage of this invention will become apparent to those skilled in the art.

SUMMARY OF THE INVENTION

It has been found that the compounds of the formula I and their physiologically acceptable acid addition salts possess valuable pharmacological properties. Thus, in particular, they are active on the central nervous system, especially as serotonin agonists and antagonists. They inhibit the binding of tritiated serotonin ligands to hippocampal receptors (Cossery et al., European J. Pharmacol. 140 (1987), 143–155). They also modify the accumulation of DOPA in the corpus striatum and the accumulation of 5-HTP in the nuclei raphes (Seyfried et al., European J. Pharmacol. 160 (1989), 31–41). Thus, compounds according to formula I can be used as commercial research tools, e.g., to identify a drug's potency at a receptor, such as the serotonin receptor, to block serotonin receptors to measure a drug's binding to other receptors, and as general neurotransmitter probes. They also have analgesic and hypotensive effects; thus, in catheterized, conscious, spontaneously hypertensive rats (strain: SHR/Okamoto/NIH-MO-CHB-Kisslegg; method: q.v. Weeks and Jones, Proc. Soc. Exptl. Biol. Med. 104 (1960), 646–648), the directly measured blood pressure is lowered after oral administration of the compounds. They are also useful for prophylaxis and control of the sequelae of cerebral infarction (Apoplexia cerebri) such as stroke and cerebral ischaemia, and for the treatment of extrapyramidal motor side effects of neuroleptics and of Parkinson's disease.

Compounds of the formula I and their physiologically acceptable acid addition salts can therefore be used as active ingredients for anxiolytics, antidepressants and/or antihypertensives, and also as intermediates for the preparation of other pharmaceutical active ingredients.

The invention relates to the indole derivatives of the formula I and to their physiologically acceptable acid addition salts.

The radical A is alkyl having 1, 2, 3, 4, 5 or 6 C atoms, especially 1 or 2 C atoms, preferably methyl and also ethyl, n-propyl, isopropyl, n-butyl, isobutyl, sec-butyl or tert-butyl. OA is preferably methoxy and also ethoxy, n-propoxy, isopropoxy, n-butoxy, isobutoxy, sec-butoxy or tert-butoxy. NHA is preferably methylamino and also ethylamino, n-propylamino, isopropylamino, n-butylamino, isobutylamino, sec-butylamino or tert-butylamino. $NA_2$ is preferably dimethylamino and also N-ethyl-N-methylamino, diethylamino, di-n-propylamino, diisopropylamino or di-n-butylamino.

Resulting from thru, CO-NHA is particularly preferably N-methylcarbamoyl or N-ethylcarbamoyl and $CO-NA_2$ is preferably N,N-dimethylcarbamoyl or N,N-diethylcarbamoyl.

The indole radicals are unsubstituted or mono- or disubstituted. Monosubstitution is preferred, the substituents preferably being in the 5-position, but can further also be in the 2-, 4-, 6- or 7-position. If both indol-3-yl radicals are substituted, the respective substituents can be identical or different. The number of substituents in the two indole radicals can also be different from one another.

Preferred substituents $R^1$, $R^2$, $R^3$ and $R^4$ on the indolyl radicals are, for example, $CO_2H$, $CO_2CH_3$, $OCH_3$, OH, $O-CH_2-O$, F, CN or $CONH_2$.

If the indole system is substituted in the 2-position, substitution there by A is particularly preferred.

The parameter n can be 2, 3, 4, 5 or 6, preferably it is 3 or 4.

$R^5$ and $R^6$ are preferably each hydrogen, but further together can also be a bond.

Accordingly, the invention relates particularly to those compounds of the formula I in which at least one of said radicals has one of the preferred meanings indicated above. Some preferred groups of compounds can be expressed by the formulae Ia to Ih below, which correspond to formula I and in which the radicals not described in greater detail are as defined for formula I, but in which:

in Ia $R^2$ and $R^4$ are H and $R^1$ and $R^3$ are identical and are each in the 5-position of the indole radicals;

in Ib $R^2$ and $R^4$ are H and $R^1$ and $R^3$ are each COOH, COOA, $CONH_2$, CONHA, $CONA_2$ or CN and are each in the 5-position of the indole radicals;

in Ic $R^2$ and $R^4$ are H and $R^1$ and $R^3$ are each OH, OA, F, Cl, Br, I or $CF_3$ and are each in the 5-position of the indole radicals;

in Id $R^1$ and $R^2$ and also $R^3$ and $R^4$ each are together methylenedioxy;

in Ie $R^2$, $R^4$, $R^5$ and $R^6$ are each H;

in If $R^2$ and $R^4$ are H and $R^5$ and $R^6$ together are a bond; $R^2$, $R^4$, $R^5$ and $R^6$ are each H and $R^1$ and $R^3$ are identical and are F, CN, OA or $CONH_2$;

in Ih $R^2$, $R^4$, $R^5$ and $R^6$ are each H and $R^1$ and $R^3$ are different from one another and are each H, COOH, COOA, $OCH_3$, OH, CN, $CONH_2$, $CONA_2$ or CONHA;

in Ii $R^1$ and/or $R^3$ are A, in particular methyl, and are in the 2-position of the indole radicals.

Especially preferred compounds, however, are those of the partial formulae Ik and Iak to Ihk, which correspond to the partial formulae Ia to Ik and to the formula I, but in which additionally n is 2, 3 or 4.

The invention further relates to a process for the preparation of piperidine derivatives of the formula I, and their salts, characterized in that a compound of the formula II

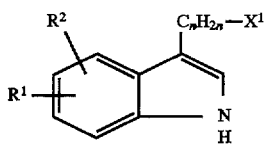

wherein $X^1$ is X or $NH_2$,

X is Cl, Br, I, OH or an OH group functionally modified to form a reactive group, and $R^1$, $R^2$ and n are as defined above, is reacted with a compound of the formula III

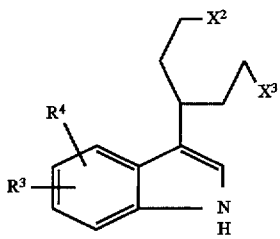

wherein $X^2$ and $X^3$ can be identical or different and are each X if $X^1=NH_2$ or are together NH in other cases, and $R^3$ and $R^4$ are as defined, or in that a compound of the formula IV

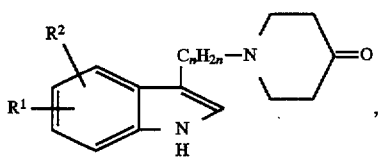

wherein $R^1$ $R^2$ and n are as defined, is reacted with an indole of the formula V

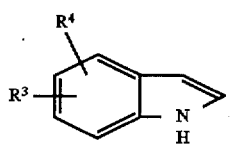

wherein $R^3$ and $R^4$ are as defined, or in that a compound of the formula I in which $R^5$ is OH and $R^6$ is H is converted into another compound of the formula I by dehydration, or in that a compound which has the formula I except that one or more hydrogen atoms have been replaced by one or more reducible groups and/or one or more additional C—C and/or C—N bonds are treated with a reducing agent, or in that a compound which has the formula I except that one or more hydrogen atoms have been replaced by one or more solvolyzable groups is treated with a solvolyzing agent, and/or in that a radical $R^1$, $R^2$, $R^3$ and/or $R^4$ is converted into an(other) radical(s) $R^1$, $R^2$, $R^3$ and/or $R^4$ by esterification, hydrolysis, etherification, ether cleavage, complete or partial hydrolysis or by alkylation and/or in that a resulting base or acid of the formula I is converted into one of its salts by treatment with an acid or base.

The compounds of the formula I are otherwise prepared by methods known per se, such as those described in the literature (e.g. in the standard works such as Houben-Weyl, Methoden der Organischen Chemie (Methods of Organic Chemistry), Georg-Thieme-Verlag, Stuttgart; Organic Reactions, John Wiley & Sons, Inc., New York; J. March, Adv. Org. Chem., 3rd Ed. J. Wiley & Sons (1985), namely under reaction conditions such as those which are known and suitable for said reactions. It is also possible to make use of variants known per se, which are not mentioned in greater detail here.

If desired, the starting materials for the claimed process can also be formed in situ in such a way that they are not isolated from the reaction mixture but are immediately reacted further to give the compounds of the formula I.

In the indole derivatives of the formula II, $X^1$ is preferably X; accordingly, in the compounds of the formula II, $X^2$ and $X^3$ are together preferably ME. The radical X is preferably Cl or Br, but it can also be I, OK or an OK group functionally modified to form a reactive group, especially alkylsulfonyloxy having 1–6 C atoms (e.g. methanesulfonyloxy) or arylsulfonyloxy having 6–10 C atoms (e.g. benzenesulfonyloxy, p-toluenesulfonyloxy, naphthalene-1- or -2-sulfonyloxy).

Accordingly, the indole derivatives of the formula I can be obtained especially by reacting 3-(chloroalkyl)-or 3-(bromoalkyl)indoles with 3-piperid-4-yl-indoles in which therefore $X^2$ and $X^3$ together are an NH group (designated as IIIa hereafter).

Some of the compounds of the formulae II and, in particular, III are known; the unknown compounds of the formulae II and III can easily be prepared analogously to the known compounds.

Primary alcohols of the formula Ind-$C_nH_{2n}$—OH, where Ind is always the indol-3-yl radical substituted by $R^1$ and $R^2$ or $R^3$ and $R^4$, can be obtained e.g. by reducing the appropriate carboxylic acids or their esters. Treatment with thionyl chloride, hydrogen bromide, phosphorus tribromide or similar halogen compounds yields the corresponding halides of the formula Ind-$C_nH_{2n}$-Hal (Hal: Br, Cl). The corresponding sulfonyloxy compounds can be obtained from the alcohols Ind-$C_nH_{2n}$—OH by reaction with the appropriate sulfonyl chlorides.

The iodine compounds of the formula I Ind-$C_nH_{2n}$—I can be obtained e.g. by reacting potassium iodide with the appropriate p-toluenesulfonic acid esters. The amines of the formula Ind-$C_nH_{2n}$—$NH_2$ can be prepared e.g. from the halides with potassium phthalimide or by reducing the appropriate nitriles.

Most of the piperazine derivatives IIIa are known and can be obtained e.g. by reacting 4-piperidinone, protected in the 1-position by customary amino protective groups known per se, with indoles which are optionally substituted by the radicals $R^3$ and/or $R^4$. Preferably, these reactions are carried out under the action of a catalyst, for example of an acid. The resulting product can then be reacted directly, after removing the protective group, with a compound of the formula II, or else dehydrated beforehand to a 1, 2, 5, 6-tetrahydropyridine derivative and then additionally hydrogenated.

The reaction of the compounds II and III proceeds according to methods such as those known from the literature for the electrophilic substitution of indoles. The components can be reacted together in the absence of a solvent, in a sealed tube or an autoclave if necessary. It is preferred, however, to react the compounds in the presence of an inert solvent. Examples of suitable solvents are hydrocarbons such as benzene, toluene or xylene; ketones such as acetone or butanone; alcohols such as methanol, ethanol, isopropanol or n-butanol; ethers such as tetrahydrofuran (THF) or dioxane; amides such as dimethylformamide (DMF) or N-methylpyrrolidone; or nitriles such as acetonitrile, or else, if desired, mixtures of these solvents with one another or mixtures with water.

The reaction time is between a few minutes and 14 days, depending on the conditions used, and the reaction temperature is between about 0° and 150°, normally between 20° and 130°.

In some cases, the addition of an acid-binding agent, for example an alkali metal or alkaline earth metal hydroxide, carbonate or bicarbonate or another alkali metal or alkaline earth metal salt of a weak acid, preferably the potassium, sodium or calcium salt, or the addition of an organic base such as triethylamine, dimethylaniline, pyridine or quinoline may favour the reaction. In other cases, the addition of catalytic amounts of an acid, preferably a mineral acid, such as e.g. HCl, is favourable.

It is also possible to obtain a compound of the formula I by reacting a compound of the formula IV with an indole derivative of the formula V.

Some of the compounds of the formulae IV and, in particular, V are known; the unknown compounds can easily be prepared analogously to the known compounds. Thus, compounds of the formula IV can easily be prepared by reaction of Ind-$C_nH_{2n}$—$NH_2$ with 1,5-dihalopentan-3-one, halogen preferably being chlorine or bromine. It is also possible to obtain compounds of type IV by reaction of Ind-$C_nH_{2n}$—Cl, Ind-$C_nH_{2n}$—Br or Ind-$C_nH_{2n}$—I with 4-piperidone.

The indoles of the formula V can be prepared by the various possibilities for the synthesis of indoles, which are known per se, for example the Fischer indole synthesis.

The reaction of the compounds IV and V proceeds according to methods which are known from the literature for the reactions of enamines with electrophilic reaction components. The components can be reacted with one another directly, without the presence of a solvent, if appropriate in a closed tube or in an autoclave, at normal pressure or at elevated pressure, an inert gas such as e.g. $N_2$ being added to increase the pressure. However, it is also possible to react the compounds in the presence of an inert solvent. Suitable solvents are those mentioned previously for the reaction of II with III.

Depending on the reaction conditions chosen, the optimum reaction time is between a few minutes and 14 days, and the reaction temperature is between about 0° and 150°, usually between 20° and 130°.

A compound of the formula I can also be obtained by treating a precursor, in which hydrogen atoms have been replaced by one or more reducible groups and/or one or more additional C—C and/or C—N bonds, with a reducing agent, preferably at temperatures of between −80° and +250°, in the presence of at least one inert solvent.

Reducible groups (groups replaceable by hydrogen) are, in particular, oxygen in a carbonyl group, hydroxyl, arylsulfonyloxy (e.g. p-toluenesnlfonyloxy), N-benzenesulfonyl, N-benzyl or O-benzyl.

In principle, compounds containing only one of the above-mentioned groups or additional bonds, or compounds containing two or more of the above-mentioned groups or additional bonds adjacent to one another, can be converted into a compound of the formula I by reduction, it being possible simultaneously to reduce substituents in the indole radicals which are present in the starting compound. This is preferably carried out using nascent hydrogen or complex metal hydrides or by means of a Wolff-Kishner reduction or the reductions with hydrogen gas under transition metal catalysis.

Preferred starting materials for the reduction have the formula VI

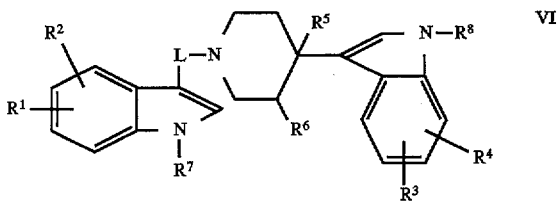

wherein $R^7$ and $R^8$ are H or, for example, arylsulfonyl groups and/or benzyl groups, L is $C_nH_{2n}$ or a chain corresponding to this radical, but wherein one or more —$CH_2$— groups are replaced by —CO—, and $R^1$, $R^2$, $R^3$, $R^4$, $R^5$ and $R^6$ are as defined, n is, preferably, 2–6.

but in which $R^7$ and $R^8$ cannot simultaneously be H and L $C_nH_{2n}$.

In the compounds of the formula VI, L is preferably —CO—$(CH_2)_{n-2}$—CO— [specifically —COCO—, —COCH$_2$CO—, —CO—$(CH_2)_2$—CO—, —CO—$(CH_2)_3$—CO—], —$(CH_2)_{n-1}$—CO— [specifically —CH$_2$—CO—, —CH$_2$CH$_2$—CO—, —$(CH_2)_3$—CO— or —$(CH_2)_4$—CO—], further examples being —CO—CH$_2$CH$_2$—, —CO—$(CH_2)_3$—, —CH$_2$—CO—CH$_2$CH$_2$—, —CH$_2$CH$_2$—CO—CH$_2$—, —CO—$(CH_2)_4$—, —CH$_2$—CO—$(CH_2)_3$—, —CH$_2$CH$_2$—CO—CH$_2$CH$_2$— or —$(CH_2)_3$—CO—CH$_2$—.

Compounds of the formula VI can be prepared e.g. by reacting compounds of the formula III, which were optionally substituted beforehand in the 1-position, with a compound of the formula VII

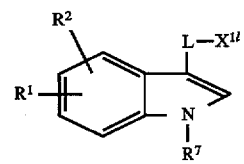

wherein $R^1$, $R^2$, $R^7$, L and $X^1$ are as defined above, under the conditions indicated above for the reaction of II with III.

If nascent hydrogen is used as the reducing agent, this can he produced e.g. by treating metals with weak acids or with bases. Thus it is possible e.g. to use a mixture of zinc with an alkali metal hydroxide solution or a mixture of iron with acetic acid. It is also appropriate to use sodium or another alkali metal in an alcohol such as ethanol, isopropanol, butanol, amyl or isoamyl alcohol or phenol. It is also possible to use an aluminum-nickel alloy in aqueous-alkaline solution, ethanol being added if necessary. Sodium amalgam or aluminum amalgam in aqueous-alcoholic or aqueous solution is also suitable for producing the nascent hydrogen. The reaction can also be carried out in the heterogeneous phase, in which case it is convenient to use an aqueous phase and a benzene or toluene phase.

Other reducing agents which can be used to particular advantage are complex metal hydrides such as LiAlH$_4$, NABH$_4$, diisobutylaluminium hydride or NaAl(OCH$_2$CH$_2$OCH$_3$)$_2$H$_2$, and diborane, catalysts such as BF$_3$, AlCl$_3$ or LiBr being added if desired. Solvents which are suitable for this purpose are, in particular, ethers such as diethyl ether, di-n-butyl ether, THF, dioxane, diglyme or 1,2-dimethoxyethane, and hydrocarbons such as benzene.

Solvents which are suitable for a reduction with NaBH$_4$ are primarily alcohols such as methanol or ethanol, as well as water and aqueous alcohols. Reduction by these methods is preferably carried out at temperatures of between −80° and +150°, especially of between about 0° and about 100°.

The reduction of —CO groups in acid amides (e.g. those of the formula VI in which L is a —(CH$_2$)$_{n-1}$—CO group) to CH$_2$ groups can be carried out to particular advantage with LiAlH$_4$ in THF at temperatures of between about 0° and 66°. Arylsulfonyl protecting groups located in the 1-position of the indole ring can be simultaneously eliminated by reduction. N-Benzyl groups can be eliminated by reduction with sodium in liquid ammonia.

It is also possible to reduce one or more carbonyl groups to CH$_2$ groups according to the Wolff-Kishner method, e.g. by treatment with anhydrous hydrazine in absolute ethanol, under pressure, at temperatures of between about 150° and 250°. A sodium alcoholate is advantageously used as the catalyst. The reduction can also be varied according to the Huang-Minlon method by carrying out the reaction with hydrazine hydrate in a high-boiling water-miscible solvent such as diethylene glycol or triethylene glycol, in the presence of an alkali such as sodium hydroxide. The reaction mixture is normally boiled for about 3–4 hours. The water is then distilled off and the hydrazone formed is decomposed at temperatures of up to about 200°. The Wolff-Kishner reduction can also be carried out with hydrazine in dimethyl sulfoxide at room temperature.

Moreover, it is possible to carry out certain reductions by using H$_2$ gas under the catalytic action of transition metals, such as e.g. Raney Ni or Pd. In this way, e.g. Cl, Br, I, SH or, in certain cases, even OH groups can be replaced by hydrogen. Nitro groups can also be converted into NH$_2$ groups by catalytic hydrogenation with Pd/H$_2$ in methanol.

Compounds which have formula I except that one or more H atoms have been replaced by one or more solvolyzable groups can be solvolyzed, especially hydrolyzed, to give the compounds of the formula I.

The starting materials for the solvolysis can be obtained for example by reacting IIIa with compounds which have formula II (X$^1$=X) except that one or more H atoms have been replaced by one or more solvolyzable groups. Thus, in particular, 1-acylindole derivatives (which have the formula I except that, in the 1-position of the indole radical, they contain an acyl group, preferably an alkanoyl, alkylsulfonyl or arylsulfonyl group having up to 10 C atoms in each case, such as methanesulfonyl, benzenesulfonyl or p-toluenesulfonyl) can be hydrolyzed to give the corresponding indole derivatives unsubstituted in the 1-position of the indole ring, e.g. in an acidic or, preferably, neutral or alkaline medium at temperatures of between 0° and 200°. Sodium, potassium or calcium hydroxide, sodium or potassium carbonate, or ammonia, is conveniently used as the base. The chosen solvents are preferably water; lower alcohols such as methanol or ethanol; ethers such as THF or dioxane; sulfones such as tetramethylene sulfone; or mixtures thereof, especially mixtures containing water. Hydrolysis can also be carried out simply by treatment with water alone, especially at the boiling point.

A compound of the formula I can furthermore be converted to another compound of the formula I by methods known per se.

Compounds of the formula I in which the indole system is substituted, e.g. by COOA, CONH$_2$, CONHA, CONA$_2$, can be obtained by derivatizing appropriate carboxyindol-3-yl compounds. It is possible, e.g. to esterify the acids or their reactive derivatives, such as e.g. their acid halides or anhydrides, with appropriate alcohols or alcoholates, using the methods known per se or one of the numerous variants. It is also possible to amidate acids, acid halides or esters with primary or secondary, aliphatic or cyclic amines. It is preferred to react the free carboxylic acid with the amine under the conditions of a peptide synthesis. This reaction is preferably carried out in the presence of a dehydrating agent, e.g. a carbodiimide such as dicyclohexylcarbodiimide or else N-(3-dimethylaminopropyl)-N-ethylcarbodiimide, or propanephosphonic anhydride (q.v. Angew. Chem. 92, 129 (1980)), diphenylphosphoryl azide or 2-ethoxy-N-ethoxycarbonyl-1,2-dihydroquinoline, in an inert solvent, e.g. a halogenated hydrocarbon such as methylene chloride, an ether such as THF or dioxane, an amide such as DMF or dimethylacetamide, or a nitrile such as acetonitrile, at temperatures of between about −10° and 40°, preferably of between 0° and 30°. Instead of the acid or amide, it is also possible to use reactive derivatives of these substances in the reaction, e.g. those in which reactive groups are blocked by protecting groups in an intermediate step. The acids can also be used in the form of their activated esters, which are conveniently formed in situ, e.g. by the addition of 1-hydroxybenztriazole or N-hydroxysuccinimide.

Furthermore, cyano-substituted indol-3-yl radicals can be hydrolyzed to give carboxy-indol-3-yl or carbamido-indol-3-yl radicals.

Compounds of the formula I in which the indole radicals are mono- or disubstituted by O-alkyl can be subjected to ether cleavage, the corresponding hydroxy derivatives being formed. It is possible, e.g. to cleave the ether groups by treatment with dimethyl sulfide-boron tribromide complex, for example in toluene, ethers such as THF or dimethyl sulfoxide, or by melting with pyridine or aniline hydrohalides, preferably pyridine hydrochloride, at about 150°–250°.

The compounds of the formula I can optionally possess a center of asymmetry. When prepared, they can therefore be obtained as racemates or else in the optically active form if optically active starting materials are used. If desired, the racemates obtained can be mechanically or chemically resolved into their optical antipodes by methods known per se. Preferably, diastereoisomers are formed from the racemate by reaction with an optically active resolving agent. Examples of suitable resolving agents are optically active acids such as the D and L forms of tartaric acid, dibenzoyltartaric acid, diacetyltartaric acid, camphorsulfonic acids, mandelic acid, malic acid or lactic acid. The different forms of the diastereoisomers can be resolved in a manner known per se, e.g. by fractional crystallization, and the optically active compounds of the formula I can be liberated from the diastereoisomers in a manner known per se.

A base of the formula I obtained can be converted with an acid into the corresponding acid addition salt. Acids which produce physiologically acceptable salts are suitable for this reaction. Thus it is possible to use inorganic acids, e.g. sulfuric acid, hydrohalic acids such as hydrochloric acid or hydrobromic acid, phosphoric acids such as orthophosphoric acid, nitric acid and sulfamic acid, as well as organic acids, i.e. specifically aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids and laurylsulfuric acid.

If desired, the free bases of the formula I can be liberated from their salts by treatment with strong bases such as sodium or potassium hydroxide or sodium or potassium carbonate provided there are no other acid groups in the molecule. In those cases where the compounds of the formula I have free acid groups, salt formation can also be achieved by treatment with bases. Suitable bases are alkali metal hydroxides, alkaline earth metal hydroxides or organic bases in the form of primary, secondary or tertiary amines.

The invention further relates to the use of the compounds of the formula I and their physiologically acceptable salts for the manufacture of pharmaceutical preparations, especially by a non-chemical route. For this purpose, they can be converted into a suitable dosage form together with at least one excipient or adjunct and, if appropriate, in combination with one or more additional active ingredients.

The invention further relates to compositions, especially pharmaceutical preparations, containing at least one compound of the formula I and/or one of their physiologically acceptable salts. These preparations can be used as drugs in human or veterinary medicine. Possible excipients are organic or inorganic substances which are suitable for enteral (e.g. oral), parenteral or topical administration and which do not react with the novel compounds, examples of such excipients being water, vegetable oils, benzyl alcohols, polyethylene glycols, gelatin, carbohydrates such as lactose or starch, magnesium stearate, talc and petroleum jelly. Tablets, coated tablets, capsules, syrups, juices, drops or suppositories are used in particular for enteral administration, solutions, preferably oily or aqueous solutions, as well as suspensions, emulsions or implants are used for parenteral administration, and ointments, creams or powders are used for topical administration. The novel compounds can also be lyophilized and the resulting lyophilizates used e.g. to manufacture injectable preparations.

The preparations indicated can be sterilized and/or can contain adjuncts such as lubricants, preservatives, stabilizers and/or wetting agents, emulsifiers, salts for influencing the osmotic pressure, buffer substances, colourants, taste correctors and/or flavourings. If desired, they can also contain one or more additional active ingredients, e.g. one or more vitamins.

The compounds of the formula I and their physiologically acceptable salts can be used for the therapeutic treatment of the human or animal body and for controlling diseases. They can be used for treating extrapyramidal motor side-effects of neuroleptics, disorders of the central nervous system, such as tension, depressions and/or psychoses, and side-effects in the treatment of hypertension (e.g. with α-methyldopa). The compounds can also be used in endocrinology and gynaecology, e.g. for the therapeutic treatment of acromegaly, hypogonadism, secondary amenorrhoea, premenstrual syndrome and undesired puerperal lactation, and also for the prophylaxis and therapy of cerebral disorders (e.g. migraine), especially in geriatrics in a manner similar to certain ergot alkaloids and for controlling the sequelae of cerebral infarction (Apoplexia cerebri), such as stroke and cerebral ischaemia.

In these treatments, the substances of the invention are normally administered analogously to known, commercially available preparations, e.g. bromocriptine, dihydroergocornine, preferably in dosages of about 0.2–500 mg, especially 0.2–50 mg per dosage unit. The daily dosage is preferably about 0.001–10 mg/kg of body weight. The low dosages (about 0.2–1 mg per dosage unit; about 0.001–0.005 mg/kg of body weight) are particularly suitable for use as anti-migraine preparations; dosages of about 10–50 mg per dosage unit are preferred for the other indications. However, the particular dose for each individual patient depends on a very wide variety of factors, for example the activity of the particular compound used, age, body weight, general state of health, sex, diet, time and method of administration, rate of excretion, drug combination and severity of the particular disease to which the therapy is applied. Oral administration is preferred. While the above dosages are for oral administration, dosages for other routes, e.g., intra/muscular or intravenous, can be determined routinely.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees. Celsius and unless otherwise indicated, all parts and percentages are by weight.

The entire disclosures of all applications, patents and publications, cited above and below, and of corresponding German application P 4414113.0 are hereby incorporated by reference.

EXAMPLES

In the following Examples, "working-up in conventional manner" means: Water is added if necessary, extraction is carried out with methylene chloride, the organic phase is separated off, dried over sodium sulfate and filtered, the filtrate is evaporated and the residue is purified by chromatography on silica gel and/or by crystallization. Temperatures are given in °C.

Example 1

1.2 g of 3-(4-chlorobutyl)-5-methoxyindole [obtainable by reaction of 5-methoxyindole with 4-chlorobutyryl chloride to give 3-(4-chlorobutyryl)-5-methoxyindole and subsequent reduction with diborane] and 1.0 g of 4-(indol-3-yl)piperidine [obtainable by reaction of N-BOC-4-piperidone with indole, subsequent dehydration and hydrogenation of the resulting double bond, and removal of the protective group] are dissolved in 200 ml of acetonitrile and the mixture is stirred at room temperature for 8 hours. Working-up in a conventional manner gives 3-[1-(4-(5-methoxyindol-3-yl)-butyl)-4-piperidyl]indole, hydrochloride, m.p. 138°–141° (dec.).

The following are obtained analogously by reaction of methyl 3-(4-chlorobutyl)indole-5-carboxylate with 4-(5-methoxyindol-3-yl)piperidine:

3-[1-(4-(5-methoxycarbonylindol-3-yl)butyl)-4-piperidyl]-5-methoxyindole, hydrochloride, m.p. 222°–224°;

of 3-(4-chlorobutyl)indole with 4-(5-methoxyindol-3-yl) piperidine:

3-[1-(4-(indol-3-yl)butyl)-4-piperidyl]-5-methoxyindole, hydrochloride, m.p. 213°–216°;

of 3-(4-chlorobutyl)-5-methoxyindole with 4-(5,6-methylenedioxyindol-3-yl)piperidine:

3-[1-(4-(5-methoxyindol-3-yl)butyl)-4-piperidyl]-5,6-methylenedioxyindole, hydrochloride, m.p. 144°–146°;

of 3-(4-chlorobutyl)-5-methoxyindole with 4-(5-methoxyindol-3-yl)piperidine:

3-[1-(4-(5-methoxyindol-3-yl)butyl)-4-piperidyl]-5-methoxyindole;
of 3-(4-chlorobutyl)indole with 4-(3-indolyl)piperidine:

3-[1-(4-(indol-3-yl)butyl)-4-piperidyl]indole;
of 3-(4-chlorobutyl)-5-methoxyindole with 4-(5-hydroxyindol-3-yl)piperidine:

3-[1-(4-(5-methoxyindol-3-yl)butyl)-4-piperidyl]-5-hydroxyindole, m.p. 203°–204°;
of 3-(4-chlorobutyl)-5-cyanoindole with 4-(5-carbamoylindol-3-yl)piperidine:

3-[1-(4-(5-cyanoindol-3-yl)butyl)-4-piperidyl]indole-5-carboxamide, hemihydrate, m.p. 227°–228°;
of 3-(4-chlorobutyl)-5-cyanoindole with 4-(5-cyanoindol-3-yl)piperidine:

3-[1-(4-(5-cyanoindol-3-yl)butyl)-4-piperidyl]-5-cyanoindole, dihydrate, m.p. 95°–101°;
of 3-(4-chlorobutyl)-5-methoxycarbonylindole with 4-(5-carbamoylindol-3-yl)piperidine:

3-[1-(4-(5-methoxycarbonylindol-3-yl)butyl)-4-piperidyl]indole-5-carboxamide, hydrate, m.p. 228°–231°;
of 3-(4-chlorobutyl)indole-5-carboxamide with 4-(5-carbamoylindol-3-yl)piperidine:

3-[1-(4-(5-carbamoylindol-3-yl)butyl)-4-piperidyl]indole-5-carboxamide, trihydrochloride, m.p. 202°–203°;
of 3-(4-chlorobutyl)-5-fluoroindole with 4-(5-fluoroindol-3-yl)piperidine:

3-[1-(4-(5-fluoroindol-3-yl)butyl)-4-piperidyl]-5-fluoroindole;
of methyl 3-(4-chlorobutyl)indole-5-carboxylate with 4-(5-methoxycarbonylindol-3-yl)piperidine:

methyl 3-[1-(4-(5-methoxycarbonylindol-3-yl) butyl)-4-piperidyl]indole-5-carboxylate;
of 3-(4-chlorobutyl)indole-5-carboxamide with 4-(5-cyanoindol-3-yl)piperidine:

3-[1-(4-(5-carbamoylindol-3-yl)butyl)-4-piperidyl]-5-cyanoindole.

Example 2

0.8 g of methyl 3-[1-(4-(5-methoxycarbonylindol-3-yl)butyl)-4-piperidyl]indole-5-carboxylate [obtainable according to Example 1] is boiled for 0.5 h with 100 ml of 2N ethanolic KOH, worked up in a conventional manner and 3-[1-(4-(5-carboxyindol-3-yl)butyl)-4-piperidyl]-indole-5-carboxylic acid is obtained.

The following are obtained analogously by hydrolysis of the corresponding ester starting
from 3-[1-(4-(5-methoxycarbonylindol-3-yl)butyl)-4-piperidyl]-5-methoxyindole:

3-[1-(4-(5-carboxyindol-3-yl)butyl)-4-piperidyl]-5-methoxyindole, hydrochloride hydrate, m.p. 248° (dec.);
from 3-[1-(4-(5-methoxycarbonylindol-3-yl)butyl)-4-piperidyl]indole-5-carboxamide:

3-[1-(4-(5-carboxyindol-3-yl)butyl)-4-piperidyl]indole-5-carboxamide, hydrochloride, m.p. 282°–285°.

Example 3

Analogously to Example 1, starting from 3-(3-chlorophenyl)-5-methoxyindole [obtainable by reaction of 5-methoxyindole with 3-chloropropionyl chloride to give 3-(3-chloropropionyl)-5-methoxyindole and subsequent reduction with diborane] and 1.0 g of 4-(indol-3-yl) piperidine [obtainable by reaction of N-BOC-4-piperidone with indole, subsequent dehydration and hydrogenation of the resulting double bond, and removal of the protective group] gives, after working-up in a conventional manner, 3-[1-(3-(5-methoxyindol-3-yl)propyl)-4-piperidyl]indole.

The following are obtained analogously by reaction of methyl 3-(3-chloropropyl)indole-5-carboxylate with 4-(5-methoxyindol-3-yl)piperidine:

3-[1-(3-(5-methoxycarbonylindol-3-yl)propyl)-4-piperidyl]-5-methoxyindole;
of 3-(3-chloropropyl)indole with 4-(5-methoxy-3-yl) piperidine:

3-[1-(3-(indol-3-yl)propyl)-4-piperidyl]-5-methoxyindole, hydrochloride;
of 3-(3-chloropropyl)-5-methoxyindole with 4-(5,6-methylenedioxyindol-3-yl)piperidine:

3-[1-(3-(5-methoxyindol-3-yl)propyl)-4-piperidyl]-5,6-methylenedioxyindole;
of 3-(3-chloropropyl)-5-methoxyindole with 4-(5-methoxyindol-3-yl)piperidine:

3-[1-(3-(5-methoxyindol-3-yl)propyl)-4-piperidyl]-5-methoxyindole;
of 3-(3-chloropropyl)indole with 4-(3-indolyl)piperidine:

3-[1-(3-(indol-3-yl)propyl)-4-piperidyl]indole;
of 3-(3-chloropropyl)-5-methoxyindole with 4-(5-hydroxyindol-3-yl)piperidine:

3-[1-(3-(5-methoxyindol-3-yl)propyl)-4-piperidyl]-5-hydroxyindole;
of 3-(3-chloropropyl)-5-cyanoindole with 4-(5-carbamoylindol-3-yl)piperidine:

3-[1-(3-(5-cyanoindol-3-yl)propyl)-4-piperidyl]indole-5-carboxamide;
of 3-(3-chloropropyl)-5-cyanoindole with 4-(5-cyanoindol-3-yl)piperidine:

3-[1-(3-(5-cyanoindol-3-yl)propyl)-4-piperidyl]-5-cyanoindole;
of 3-(3-chloropropyl)-5-methoxycarbonylindole with 4-(5-carbamoylindol-3-yl)piperidine:

3-[1-(3-(5-methoxycarbonylindol-3-yl)propyl)-4-piperidyl]indole-5-carboxamide, m.p. 195°–196°;
of 3-(3-chloropropyl)indole-5-carboxamide with 4-(5-carbamoylindol-3-yl)piperidine:

3-[1-(3-(5-carbamoylindol-3-yl)propyl)-4-piperidyl]indole-5-carboxamide, sesquihydrochloride isopropanolate, m.p. 102°–105° (dec.);
of 3-(3-chloropropyl)-5-fluoroindole with 4-(5-fluoroindol-3-yl)piperidine:

3-[1-(3-(5-fluoroindol-3-yl)propyl)-4-piperidyl]-5-fluoroindole, hydrochloride hemihydrate, m.p. 164°–165°;
of 3-(3-chloropropyl)-5-fluoroindole with 4-(6-fluoroindol-3-yl)piperidine:

3-[1-(3-(5-fluoroindol-3-yl)propyl)-4-piperidyl]-6-fluoroindole, hydrochloride hydrate, m.p. 274°–278°;
of 3-(3-chloropropyl)-5-fluoroindole with 4-(4-fluoroindol-3-yl)piperidine:

3-[1-(3-(5-fluoroindol-3-yl)propyl)-4-piperidyl]-4-fluoroindole, hydrochloride, m.p. 269°–270°;
of methyl 3-(3-chloropropyl)indole-5-carboxylate with 4-(5-methoxycarbonylindol-3-yl)piperidine:

methyl 3-[1-(3-(5-methoxycarbonylindol-3-yl)propyl)4-piperidyl]indole-5-carboxylate;
of 3-(3-chloropropyl)indole-5-carboxamide with 4-(5-cyanoindol-3-yl)piperidine:

3-[1-(3-(5-carbamoylindol-3-yl)propyl)-4-piperidyl]-5-cyanoindole, hydrate, m.p. 102°–104° (dec.).

Example 4

Analogously to Example 2, hydrolysis of methyl 3-[1-(3-(5-methoxycarbonylindol-3-yl)propyl)-4-piperidyl]indole-5-carboxylate gives 3-[1-(3-(5-carboxyindol-3-yl)propyl)-4-piperidyl]indole-5-carboxylic acid.

The following are obtained analogously by hydrolysis of the corresponding esters starting from 3-[1-(3-(5-methoxycarbonylindol-3-yl)propyl-4-piperidyl]-5-methoxyindole:

3-[1-(3-(5-carboxyindol-3-yl)propyl)-4-piperidyl]-5-methoxyindole;

from methyl 3-[1-(3-(5-methoxyindol-3-yl)propyl)-4-piperidyl]indole-5-carboxylate:

3-[1-(3-(5-methoxyindol-3-yl)propyl)-4-piperidyl]indole-5-carboxylate;

from methyl 3-[1-(3-(6-methoxyindol-3-yl)propyl)-4-piperidyl]indole-5-carboxylate:

3-[1-(3-(6-methoxyindol-3-yl)propyl)-4-piperidyl]indole-5-carboxylate;

from methyl 3-[1-(3-(4-methoxyindol-3-yl)propyl)-4-piperidyl]indole-5-carboxylate:

3-[1-(3-(4-methoxyindol-3-yl)propyl)-4-piperidyl]indole-5-carboxylic acid;

from 3-[1-(3-(5-methoxycarbonylindol-3-yl)propyl)-4-piperidyl]indole-5-carboxamide:

3-[1-(3-(5-carboxyindol-3-yl)propyl)-4-piperidyl]indole-5-carboxamide, hydrochloride, m.p. 278°–280°.

Example 5

2.1 g of 3-[1-(4-(5-methoxyindol-3-yl)butyl)-4-piperidyl] indole-5-carboxylic acid are suspended in 100 ml of N-methylpyrrolidone. 3.2 g of 2-chloro-1-methylpyridinium methanesulfonate are then added and the mixture is stirred at room temperature for 12 hours. Dried $NH_3$ gas is passed into the resulting solution until it is saturated and it is stirred again for 10 hours. Working-up in a conventional manner gives 3-[1-(4-(5-methoxyindol-3-yl)butyl)-4-piperidyl] indole-5-carboxamide.

The following are obtained analogously by amidation of the following carboxylic acids with 2-chloro-1-methylpyridinium methanesulfonate:

from 3-[1-(4-(6-methoxyindol-3-yl)butyl)-4-piperidyl] indole-5-carboxylic acid:

3-[1-(4-(6-methoxyindol-3-yl)butyl)-4-piperidyl]indole-5-carboxamide;

from 3-[1-(4-(4-methoxyindol-3-yl)butyl)-4-piperidyl] indole-5-carboxylic acid:

3-[1-(4-(4-methoxyindol-3-yl)butyl)-4-piperidyl]indole-5-carboxamide;

from 3-[1-(3-(5-carboxyindol-3-yl)propyl)-4-piperidyl] indole-5-carboxylic acid:

3-[1-(3-(5-carbamoylindol-3-yl)propyl-4-piperidyl] indole-5-carboxamide from 3-[1-(3-(5-carboxyindol-3-yl)propyl)-4-piperidyl]-5-methoxyindole:

3-[1-(3-(5-carbamoylindol-3-yl)propyl)-4-piperidyl]-5-methoxyindole;

from 3-[1-(3-(5-methoxyindol-3-yl)propyl)-4-piperidyl] indole-5-carboxylic acid:

3-[1-(3-(5-methoxyindol-3-yl)propyl)-4-piperidyl] indole-5-carboxamide;

from 3-[1-(3-(6-methoxyindol-3-yl)propyl)-4-piperidyl] indole-5-carboxylic acid:

3-[1-(3-(6-methoxyindol-3-yl)propyl)-4-piperidyl] indole-5-carboxamide;

from 3-[1-(3-(4-methoxyindol-3-yl)propyl)-4-piperidyl] indole-5-carboxylic acid:

3-[1-(3-(4-methoxyindol-3-yl)propyl)-4-piperidyl] indole-5-carboxamide.

Example 6

A solution of 3.9 g of 3-[1-(4-(5-carboxyindol-3-yl)butyl)-4-piperidyl]indole-5-carboxylic acid in 250 ml of DMF is treated with 1 g of N-methylmorpholine. A solution of two equivalents of tert-butylamine in 5 ml of DMF, 1.3 g of 1-hydroxybenzotriazole and a solution of 1.9 g of N-(3-dimethylaminopropyl)-N'-ethylcarbodiimide hydrochloride in 20 ml of DMF are added with stirring. The mixture is stirred for 16 hours at room temperature and the filtrate is evaporated. Working-up in a conventional manner gives 3-[1-(4-(5-N-tert-butylcarbamoylindol-3-yl)butyl)-4-piperidyl]indole-5-N-tert-butylcarboxamide.

The following are obtained analogously by reaction with tert-butylamine starting from 3-[1-(4-(5-carboxyindol-3-yl)butyl-4-piperidyl]-5-methoxyindole:

3-[1-(4-(5-N-tert-butylcarbamoylindol-3-yl)butyl)-4-piperidyl]-5-methoxyindole;

from 3-[1-(4-(5-carboxyindol-3-yl)butyl)-4-piperidyl] indole-5-carboxamide:

3-[1-(4-(5-N-tert-butylcarbamoylindol-3-yl)butyl)-4-piperidyl]indole-5-carboxamide;

from 3-[1-(3-(5-carboxyindol-3-yl)propyl)-4-piperidyl]-5-methoxyindole:

3-[1-(3-(5-N-tert-butylcarbamoylindol-3-yl)propyl)-4-piperidyl]-5-methoxyindole.

Example 7

A mixture of 1.6 g of 3-[1-(4-(indol-3-yl)butyl)-4-piperidyl]-5-methoxyindole [which can be prepared according to Example 1], 1.8 g of pyridine hydrochloride and 50 ml of pyridine is boiled for 3 hours. The mixture is cooled, the solvent is evaporated and the residue is worked up in a conventional manner and gives 3-[1-(4-(indol-3-yl)butyl)-4-piperidyl]-5-hydroxyindole, m.p. 178°–180°.

The following are obtained analogously from 3-[1-(4-(5-methoxyindol-3-yl)butyl-4-piperidyl] indole:

3-[1-(4-(5-hydroxyindol-3-yl)butyl)-4-piperidyl]indole;

from 3-[1-(4-(5-methoxyindol-3-yl)butyl)-4-piperidyl]-5-methoxyindole:

3-[1-(4-(5-hydroxyindol-3-yl)butyl)-4-piperidyl]-5-hydroxyindole;

from 3-[1-(4-(6-methoxyindol-3-yl)butyl)-4-piperidyl]-5-hydroxyindole:

3-[1-(4-(6-hydroxyindol-3-yl)butyl)-4-piperidyl]-5-hydroxyindole;

from 3-[1-(3-indol-3-yl)propyl-4-piperidyl]-5-methoxyindole:

3-[1-(3-(indol-3-yl)propyl-4-piperidyl]-5-hydroxyindole;

from 3-[1-(3-(5-methoxyindol-3-yl)propyl)-4-piperidyl]-5-methoxyindole:

3-[1-(3-(5-hydroxyindol-3-yl)propyl-4-piperidyl]-5-hydroxyindole.

Example 8

A solution of 3.6 g of 3-[1-(4-(5-methoxycarbonylindol-3-yl)butyl)-4-piperidyl]indole in 40 ml of THF is added dropwise to a suspension of 0.6 g of lithium aluminum hydride in 20 ml of THF with stirring. The mixture is then stirred for a further hour at 25°, 20 ml of dilute sodium hydroxide solution are added, the mixture is filtered and the filtrate is worked up in a conventional manner. 3-[1-(4-(5-hydroxymethylindol-3-yl)butyl)-4-piperidyl]indole is obtained.

The following are obtained analogously by reduction of 3-[1-(4-(5-methoxycarbonylindol-3-yl)butyl)-4-piperidyl]-5-methoxyindole:

3-[1-(4-(5-hydroxymethylindol-3-yl)butyl)-4-piperidyl]-5-methoxyindole;

of methyl 3-[1-(4-(5-methoxycarbonylindol-3-yl)butyl)-4-piperidyl]indole-5-carboxylate:

3-[1-(4-(5-hydroxymethylindol-3-yl)butyl)-4-piperidyl]-5-hydroxymethylindole;

of 3-[1-(3-(5-methoxycarbonylindol-3-yl)propyl)-4-piperidyl]-5-methoxyindole:

3-[1-(3-(5-hydroxymethylindol-3-yl)propyl)-4-piperidyl]-5-methoxyindole;

of 3-[1-(3-(5-methoxycarbonylindol-3-yl)propyl)-4-piperidyl]indole-5-carboxamide:

3-[1-(3-(5-hydroxymethylindol-3-yl)propyl)-4-piperidyl]indole-5-carboxamide.

Example 9

HCl gas is passed into a boiling solution of 2.5 g of 3-[1-(4-(5-carboxyindol-3-yl)butyl)-4-piperidyl]-5-fluoroindole in 50 ml of absolute methanol for hours. The mixture is then boiled for a further hour, is worked up in a conventional manner and gives 3-[1-(4-(5-methoxycarbonylindol-3-yl)butyl)-4-piperidyl]-5-fluoroindole.

Example 10

Analogously to Example 1, reaction of 3-(4-chlorobutyl)indole [obtainable by reaction of indole with 4-chlorobutyryl chloride to give 3-(4-chlorobutyryl)-indole and subsequent reduction with diborane] with 4-(indol-3-yl)-1,2,5,6-tetrahydropyridine [obtainable by reaction of N-BOC-4-piperidone with-indole and subsequent dehydration, and removal of protective group] in 200 ml of acetonitrile gives, after working up in a conventional manner, 3-[1-(4-(indol-3-yl)butyl)-1,2,5,6-tetrahydropyrid-4-yl]indole, hydrochloride, m.p. 190°–192°.

The following are obtained analogously by reaction of methyl 3-(4-chlorobutyl)indole-5-carboxylate with 4-(5-methoxyindol-3-yl)-1,2,5,6-tetrahydropyridine:

3-[1-(4-(5-methoxycarbonylindol-3-yl)butyl)-1,2,5,6-tetrahydropyrid-4-yl]-5-methoxyindole;

of 3-(4-chlorobutyl)indole with 4-(5-methoxyindol-3-yl)-1,2,5,6-tetrahydropyridine:

3-[1-(4-(indol-3-yl)butyl)-1,2,5,6-tetrahydropyrid-4-yl]-5-methoxyindole;

of 3-(4-chlorobutyl)-5-methoxyindole with 4-(5,6-methylenedioxyindol-3-yl)-1,2,5,6-tetrahydropyridine:

3-[1-(4-(5-methoxyindol-3-yl)butyl)-1,2,5,6-tetrahydropyrid-4-yl]-5,6-methylenedioxyindole;

of 3-(4-chlorobutyl)-5-methoxyindole with 4-(5-methoxyindol-3-yl)-1,2,5,6-tetrahydropyridine:

3-[1-(4-(5-methoxyindol-3-yl)butyl)-1,2,5,6-tetrahydropyrid-4-yl]-5-methoxyindole;

of 3-(4-chlorobutyl)indole with 4-(3-indolyl)-1,2,5,6-tetrahydropyridine:

3-[1-(4-(indol-3-yl)butyl)-1,2,5,6-tetrahydropyrid-4-yl]indole;

of 3-(4-chlorobutyl)-5-methoxyindole with 4-(5-hydroxyindol-3-yl)-1,2,5,6-tetrahydropyridine:

3-[1-(4-(5-methoxyindol-3-yl)butyl)-1,2,5,6-tetrahydropyrid-4-yl]-5-hydroxyindole;

of 3-(4-chlorobutyl)-5-cyanoindole with 4-(5-carbamoylindol-3-yl)-1,2,5,6-tetrahydropyridine:

3-[1-(4-(5-cyanindol-3-yl)butyl)-1,2,5,6-tetrahydropyrid-4-yl]indole-5-carboxamide;

of 3-(4-chlorobutyl)-5-cyanoindole with 4-(5-cyanoindole-3-yl)-1,2,5,6-tetrahydropyridine:

3-[1-(4-(5-cyanoindol-3-yl)butyl)-1,2,5,6-tetrahydropyrid-4-yl]-5-cyanoindole;

of 3-(4-chlorobutyl)-5-methoxycarbonylindole with 4-(5-carbamoylindol-3-yl)-1,2,5,6-tetrahydropyridine:

3-[1-(4-(5-methoxycarbonylindol-3-yl)butyl)-1,2,5,6-tetrahydropyrid-4-yl]indole-5-carboxamide;

of 3-(4-chlorobutyl)indole-5-carboxamide with 4-(5-carbamoylindol-3-yl)-1,2,5,6-tetrahydropyridine:

3-[1-(4-(5-carbamoylindol-3-yl)butyl)-1,2,5,6-tetrahydropyrid-4-yl]indole-5-carboxamide;

of 3-(4-chlorobutyl)-5-fluoroindole with 4-(5-fluoroindol-3-yl)-1,2,5,6-tetrahydropyridine:

3-[1-(4-(5-fluoroindol-3-yl)butyl)-1,2,5,6-tetrahydropyrid-4-yl]-5-fluoroindole;

of methyl 3-(4-chlorobutyl)indole-5-carboxylate with 4-(5-methoxycarbonylindol-3-yl)-1,2,5,6-tetrahydropyridine:

methyl 3-[1-(4-(5-methoxycarbonylindol-3-yl)butyl)-(1,2,5,6-tetrahydropyrid-4-yl)]-5-carboxylate;

of 3-(4-chlorobutyl)indole-5-carboxamide with 4-(5-cyanoindol-3-yl)-1,2,5,6-tetrahydropyridine:

3-[1-(4-(5-carbamoylindol-3-yl)butyl)-1,2,5,6-tetrahydropyrid-4-yl]-5-cyanoindole.

Example 11

Analogously to Example 1, starting from 3-(2-chloroethyl)-2-methyl-5-methoxyindole [obtainable by reaction of 2-methyl-5-methoxyindole with 2-chloroacetyl chloride to give 3-(2-chloroacetyl)-2-methyl-5-methoxyindole and subsequent reduction with diborane] and 1.0 g of 4-(5-fluoroindol-3-yl)piperidine [obtainable by reaction of N-BOC-4-piperidone with 5-fluoroindole, subsequent dehydration and hydrogenation of the resulting double bond, and removal of the protective group] gives, after working up in a conventional manner, 3-[1-(2-(2-methyl-5-methoxyindol-3-yl)ethyl)-4-piperidyl]-5-fluoroindole, hydrochloride, Rf=0.31.

The following are obtained analogously by reaction of 3-(2-chloroethyl)indole with 4-(5-fluoroindol-3-yl)piperidine:

3-[1-(2-indol-3-yl)ethyl-4-piperidyl]-5-fluoroindole, hydrochloride, Rf=0.20;

of 3-(2-chloroethyl)indole with 4-(4-fluoroindol-3-yl)piperidine:

3-[1-(2-indol-3-yl)ethyl-4-piperidyl]-4-fluoroindole, hydrochloride, m.p. 297°;

of 3-(2-chloroethyl)-2-methyl-5-methoxyindole with 4-(4-fluoroindol-3-yl)piperidine:

3-[1-(2-(2-methyl-5-methoxy-indol-3-yl)ethyl)-4-piperidyl]-4-fluoroindole, hydrochloride, m.p, 215°;

of 3-(2-chloroethyl)indole with 4-(5-methoxyindol-3-yl)piperidine:

3-[1-(2-(indol-3-yl)ethyl)-4-piperidyl]-5-methoxyindole;

of 3-(2-chloroethyl)-2-methyl-5-methoxyindole with 4-(4-methoxyindol-3-yl)piperidine:

3-[1-(2-(2-methyl-5-methoxyindol-3-yl)ethyl)-4-piperidyl]-4-methoxyindole.

Example 12

0.4 g of 3-[1-( (5-fluoroindol-3-yl)methylcarbonyl)-4-piperidyl]-5-fluoroindole [obtainable by reaction of 5-fluoroindole with 2-chloroacetyl chloride to give 3-(2-chloroacetyl)-5-methoxyindole and subsequent reaction with 4-(5-fluoroindol-3-yl)piperidine] are dissolved in 30 ml of THF and treated dropwise at room temperature with 1.3 equivalents of NaAl(OCH$_2$CH$_2$OCH$_3$)$_2$H$_2$, dissolved in 10 ml of toluene. The mixture is stirred for 2 h at room temperature, then worked up in a conventional manner and gives 3-[1-(2-(5-fluoroindol-3-yl)ethyl)-4-piperidyl]-5-fluoroindole, hydrochloride, Rf=0.27.

The following are obtained analogously by reduction with NaAl(OCH$_2$CH$_2$OCH$_3$)$_2$H$_2$:

from 3-[1-(2-(5-fluoroindol-3-yl)ethylcarbonyl)-4-piperidyl]-4-fluoroindole:

3-[1-(3-(5-fluoroindol-3-yl)propyl)-4-piperidyl]-4-fluoroindole;

from 3-[1-((5-fluoroindol-3-yl)methylcarbonyl)-4-piperidyl]-4-fluoroindole:

3-[1-(2-(5-fluoroindol-3-yl)ethyl)-4-piperidyl]-4-fluoroindole, hydrochloride, m.p. 260°.

The following examples relate to pharmaceutical preparations:

Example A

Injection Vials

A solution of 100 g of an active ingredient of a compound of a formula I and 5 g of disodium hydrogen phosphate are adjusted to pH 6.5 using 2N hydrochloric acid in 3 l of double-distilled water, filtered under sterile conditions, filled into injection vials and lyophilized under sterile conditions and the vials are sealed under sterile conditions. Each injection vial contains 5 mg of active ingredient.

Example B

Suppositories

A mixture of 20 g of an active ingredient of the formula I is melted with 100 g of soya lecithin and 1400 g of cocoa butter, poured into molds and allowed to cool. Each suppository contains 20 mg of active ingredient.

Example C

Solution

A solution is prepared from 1 g of an active ingredient of the formula I, 9.38 g of NaH$_2$PO$_4$.2 H$_2$O, 28.48 g of Na$_2$HPO$_4$.12 H$_2$O and 0.1 g of benzalkonium chloride in 940 ml of double-distilled water. The pH is adjusted to 6.8, and the solution is made up to 1 l and sterilized by irradiation. This solution can be used in the form of eyedrops.

Example D

Ointment 500 mg of an active ingredient of the formula I are mixed with 99.5 g of petroleum jelly under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is compressed to tablets in a conventional manner so that each tablet contains 10 mg of active ingredient.

Example F

Coated Tablets

Tablets are formed by compression analogously to Example E and then covered in a conventional manner with a coating of sucrose, potato starch, talc, tragacanth and colourant.

Example G

Capsules 2 kg of active ingredient of the formula I are filled into hard gelatin capsules in a conventional manner so that each capsule contains 20 mg of the active ingredient.

Example H

Ampoules

A solution of 1 kg of active ingredient of the formula I in 60 l of double-distilled water is filtered under sterile conditions, filled into ampoules and lyophilised under sterile conditions and the ampoules are sealed under sterile conditions. Each ampoule contains 10 mg of active ingredient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed:

1. An indolylpiperidine compound of the formula I

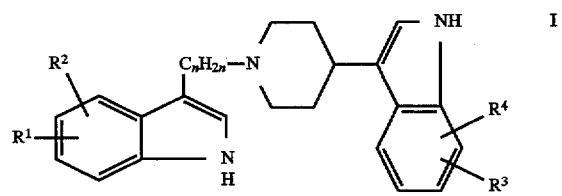

wherein $R^1$, $R^2$, $R^3$ and $R^4$ are in each case independently of one another H, OH, OA, F, Cl, Br, I, CN, or COOH, CONH$_2$, COOA, or $R^1$ and $R^2$ together and/or also $R^3$ and $R^4$ together are methylenedioxy;

n is 3 or 4, or physiologically acceptable salts thereof.

2. A compound according to claim 1, which is (a) 3-(1-(3-(5-Carbamoyl-3-indolyl)propylpiperid-4-yl) indole-5-carboxamide;

(b) 3-(1-(3-(5-carbamoyl-3-indolyl)propyl)piperid-4-yl) indole-5-carbonitrile;

(c) 3-(1-(4-(5-methoxycarbonyl-3-indolyl)butyl)piperid-4-yl)-5-methoxyindole;

(d) 3-(1-(3-(5-ethoxycarbonyl-3-indolyl)propyl)piperid-4-yl)indole-5-carboxamide; or (e) 3-(1-(4-(5-cyano-3-indolyl)butylpiperid-4-yl)indole-5-carbonitrile.

3. A compound according to claim 1, wherein
   $R^2$ and $R^4$ are H; and $R^1$ and $R^3$ are identical and are each in the 5-position of the indole group.
4. A compound according to claim 1, wherein
   $R^2$ and $R^4$ are H; and $R^1$ and $R^3$ are each COOH, COOA, $CONH_2$ or CN and are each in the 5-position of the indole group.
5. A compound according to claim 1, wherein
   $R^2$ and $R^4$ are H; and $R^1$ and $R^3$ are each OH, OA, F, Cl, Br, or I and are each in the 5-position of the indole group.
6. A compound according to claim 1, wherein
   $R^2$, $R^4$, $R^5$ and $R^6$ are each H.
7. A compound according to claim 1, wherein $R^2$, $R^4$ are each H; and $R^1$ and $R^3$ are identical and are F, CN, OA or $CONH_2$.
8. A compound according to claim 1, wherein
   $R^2$ and $R^4$, are each H; and $R^1$ and $R^3$ are different from one another and are each H, COOH, COOA, $OCH_3$, OH, CN, or $CONH_2$.
9. A compound according to claim 1, wherein n is 3.
10. A pharmaceutical composition comprising, a compound according to claim 1 and a pharmaceutically-acceptible excipient.
11. A method of treating the extrapyramidal motor side-effects caused by neuroleptics comprising, administering to a host in need thereof an effective amount of a compound according to claim 1.
12. A method of treating tension, depression, or psychoses, comprising administering to a host in need thereof an effective amount of a compound according to claim 1.
13. A process for the preparation of a 3-indolylpiperidine according to formula I of claim 1, comprising reacting a compound of the formula II

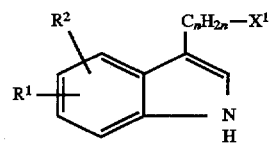

wherein
$X^1$ is X or $NH_2$,
X is Cl, Br, I, OH or an OH group functionally modified to form a reactive group, and
$R^1$, $R^2$ and n are as defined,
with a compound of the formula III

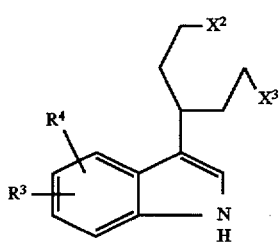

wherein $X^2$ and $X^3$ can be identical or different and are each X if $X^1=NH_2$ or are together NH in other cases, and
$R^3$ and $R^4$ are as defined.
14. A process for the preparation of a 3-indolypiperidine compound according to claim 1, comprising a compound of the formula IV

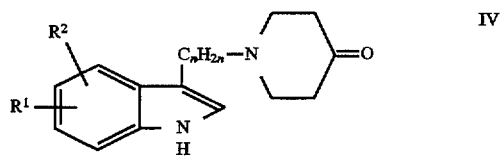

wherein $R^1$, $R^2$ and n are as defined, is reacted with an indole of the formula V

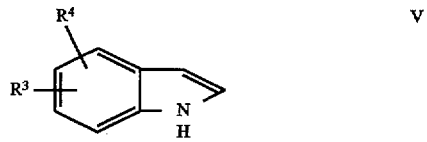

wherein $R^3$ and $R^4$ are as defined.
15. A process for the preparation of a 3-indolypiperidine compound according to claim 1, comprising converting a compound of the formula I in which $R^5$ is OH and $R^6$ is H into another compound of the formula I by dehydration, or in that a compound which has the formula I except that one or more hydrogen atoms have been replaced by one or more reducible groups and/or one or more additional C—C and/or C—N bonds is treated with a reducing agent,
or in that a compound which has the formula I except that one or more hydrogen atoms have been replaced by one or more solvolyzable groups is treated with a solvolyzing agent,
and/or in that a radical $R^1$, $R^2$, $R^3$ and/or $R^4$ is converted into an(other) radical(s) $R^1$, $R^2$, $R^3$ and/or $R^4$ by esterification, hydrolysis, etherification, ether cleavage, complete or partial hydrolysis or by alkylation
and/or in that a resulting base or acid of the formula I is converted into one of its salts by treatment with an acid or base.
16. An indolylpiperidine compound of the formula I

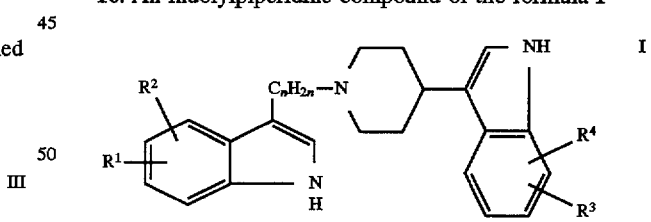

wherein
$R^1$ and $R^2$ together, and $R^3$ and $R^4$ together are methylenedioxy;
n is 3 or 4,
or physiologically acceptable salts thereof.

* * * * *